US00PP10088P

United States Patent [19]

Van Wingerden

[11] Patent Number: Plant 10,088

[45] Date of Patent: Oct. 28, 1997

[54] SAINTPAULIA PLANT NAMED 'MOONBEAM'

[75] Inventor: John Van Wingerden, Oberlin, Ohio

[73] Assignee: Green Circle Growers, Inc., Oberlin, Ohio

[21] Appl. No.: 671,568

[22] Filed: Jun. 28, 1996

[51] Int. Cl.[6] ..... A01H 5/00

[52] U.S. Cl. ..... Plt./69.2

[58] Field of Search ..... Plt./69.1, 69.2

*Primary Examiner*—James R. Feyrer
*Attorney, Agent, or Firm*—C. A. Whealy

[57] ABSTRACT

A distinctive cultivar of Saintpaulia plant named 'Moonbeam', characterized by its compact plant habit; moderate growth rate; durable dark green foliage; large dark purple frilled flowers; and numerous long-lasting flowers.

1 Drawing Sheet

The present invention relates to a new and distinct cultivar of Saintpaulia or African Violet, botanically known as *Saintpaulia ionantha*, and hereinafter referred to by the cultivar name 'Moonbeam'. It is anticipated that the plant of this application will be marketed under the Trademark "Ultra Violet". Accordingly, the plant of this application may be referred to as "Ultra Violet" 'Moonbeam' in the market place.

The new cultivar is a product of a planned breeding program conducted by the inventor in Oberlin, Ohio. The objective of the breeding program was to develop compact and durable Saintpaulia varieties with numerous, upright, long-lasting flowers and uniform flowering.

The new cultivar originated from a cross made by the inventor of the Saintpaulia cultivar 'New Orleans' (disclosed in U.S. Plant Pat. No. 5,627) with violet flowers, as the male or pollen parent, with the Saintpaulia cultivar 'Laser' (not patented) with pink frilled flowers, as the female or seed parent. The cultivar 'Moonbeam' was discovered and selected by the inventor as a flowering plant within the progeny of the stated cross in a controlled environment in Oberlin, Ohio.

In side-by-side comparisons in Oberlin, Ohio, under commercial practice, plants of the new Saintpaulia differed in flower color and were more compact in growth habit than either parent cultivar.

Asexual reproduction of the new cultivar by leaf cuttings taken at Oberlin, Ohio, has shown that the unique features of this new Saintpaulia plant are stable and reproduced true to type in successive generations of asexual reproduction.

The following traits have been repeatedly observed and are determined to be the unique characteristics of 'Moonbeam'. These characteristics in combination distinguish the new Saintpaulia plant as a new and distinct cultivar:

1. Compact plant habit.
2. Moderate growth rate.
3. Durable dark green foliage.
4. Large dark purple frilled flowers that are held upright.
5. Numerous long-lasting flowers.

The new Saintpaulia plant has not been observed under all possible environmental conditions. The phenotype may vary significantly with variations in environment such as temperature and light level, without, however, any variance in genotype.

The accompanying colored photograph illustrates the overall appearance of the new cultivar, showing the colors as true as it is reasonably possible to obtain in colored reproductions of this type. Flower and foliage colors in the photograph may appear different from the actual colors due to light reflectance. The photograph comprises a top perspective view of a typical potted plant of 'Moonbeam'.

The following observations, measurements, values, and comparisons describe plants grown in Oberlin, Ohio, under a double layer of polyethylene covering with average day and night temperatures of 21C and an average light level of 1,500 foot-candles.

In the following description, color references are made to The Royal Horticultural Society Colour Chart except where general terms of ordinary dictionary significance are used.

Classification:

*Botanical.*—*Saintpaulia ionantha* cultivar 'Moonbeam.'

*Commercial.*—Saintpaulia or African Violet.

Parentage:

*Male or pollen parent.*—*Saintpaulia ionantha* cultivar 'New Orleans' (U.S. Plant Pat. No. 5,627).

*Female or seed parent.*—*Saintpaulia ionantha* cultivar 'Laser' (not patented).

Plant description:

*Plant form.*—Leaves outwardly arching, flowers held upright and above the foliage.

*Growth habit and rate.*—Moderately vigorous, yet compact. Suitable for 10-cm containers. Time to produce a finished flowering plant in a 10-cm container from a rooted plantlet is generally 8 to 10 weeks depending on temperature, light level, and cultural practices.

*Height, soil level to top of leaves.*—About 3.5 cm.

*Height, soil level to top of flowers.*—About 8 cm.

*Distance, top of leaves to top of flowers.*—4.5 cm.

Foliage description:

*Arrangement.*—Rosette.

*Leaf appearance.*—"Girl-type" foliage, scalloped edge, dark green with characteristic pale center near the leaf base.

*Quantity of leaves.*—About 20 per 4-inch pot.

*Leaf size, largest leaves.*—Leaf length: About 6 cm. Leaf width: About 6 cm.

*Leaf shape.*—Cordate.

*Leaf tip.*—Acute.

*Leaf base.*—Cordate.

*Margin.*—Crenate, scalloped.

*Leaf surface.*—Undulating.

*Texture.*—Leathery, glossy, pubescent, durable.

*Pubescence.*—Moderate on both upper and under sides.

*Venation pattern.*—Pinnate.

*Color.*—Young foliage: Upper side: Darker than 147A. Upper, center: 187A. Under side: 147C. Venation upper side: Darker than 147A. Venation under side: 183A. Mature foliage: Upper side: Darker than 147A. Upper, center: 147C/147D/183A. Under side: 147C/147D. Venation upper side: Darker than 147A. Venation under side: 147C.

*Petiole.*—Length: About 5 cm. Diameter: About 5 mm. Shape: Tubular, wide channel on upper side towards leaf blade. Pubescence: Moderate. Aspect: Horizontal. Color: Apex: 178A. Midpoint: 178A. Base: 183A.

Flower description:

*Flower arrangement.*—Branched panicle, flowers held upright and above the foliage.

*Flower appearance.*—Semi-double, frilled, fused corolla with five petals and several petaloids. Two upper petals usually smaller than lower three petals, with a crest or tuft of petaloids at the center, but less than a full second row of petals. Flowers may appear single.

*Flower longevity.*—Individual flowers last approximately 7 to 10 days. Inflorescences are generally in flower for approximately 3 to 4 weeks under greenhouse conditions. Flowers persistent.

*Quantity of flowers per peduncle.*—Generally 7 to 10 open flowers and flower buds at a time are present, usually 3 to 4 per panicle branch.

*Flower diameter.*—About 3.75 cm.

*Flower depth, base of calyx to upper petal surface.*—About 3 mm.

*Petals.*—Appearance: Velvety, satiny. Texture: Smooth. Arrangement: Five fused into a corolla, overlapping. Upper two petals smaller than lower three petals. Several small petaloids arranged as a crest or tuft just above the center of the corolla. Shape: Ovate, rounded. Margin: Frilled or ruffled. Tip: Rounded. Size: Largest petals, length: About 2 cm. Largest petals, width: About 2 cm. Smallest petals, length: About 1.5 cm. Smallest petals, width: About 1.8 cm. Color: When opening: 89A. Upper side: Base: More purple than 89A. Center: More purple than 89A. Margins: More purple than 89A. Under side: Base: 88A. Center: 88A. Margins: 88A. Fading to: 88A.

*Petaloids.*—Arrangement: Small arranged in a tuft or crest just above the center of the corolla. Quantity: Usually 3 with the upper petaloid larger than the other two. Appearance: Velvety, satiny. Texture: Smooth. Shape: Ovate, rounded. Margin: Frilled or ruffled. Tip: Rounded. Size: Largest petaloids, length: About 1 cm. Largest petaloids, width: About 1.2 cm. Smallest petaloids, length: About 6 mm. Smallest petaloids, width: About 8 mm, Color: When opening: 89A. Upper side: Base: More purple than 89A. Center: More purple than 89A. Margins: More purple than 89A. Under side: Base: 88A. Center: 88A. Margins: 88A. Fading to: 88A.

*Peduncle.*—Length: About 6 cm. Diameter, at base: About 3 mm. Strength: Strong. Angle: Erect. Pubescence: Moderate. Color: Base: 183A. Apex: 183A.

*Flower bud, just before opening.*—Length: About 9 mm. Diameter: About 9 mm. Form or shape: Spherical. Rate of opening: Rapid. Color: Darker than 88A.

*Calyx/sepals.*—Calyx shape: Star-shaped. Calyx size: Height: About 7 mm. Width: About 1 cm. Sepal shape: Linear. Sepal arrangement: Fused at base. Sepal size: Length: About 6 mm. Width: About 2 mm. Sepal texture: Pubescent. Sepal number: 5. Sepal margin: Entire. Sepal tip: Pointed. Sepal color: Upper side: 146A. Under side: 187A.

*Stamens, mature flower.*—Stamen number: 2. Anther size: Length: About 2 mm. Width: About 3 mm. Height: About 2 mm. Anther color: 7A. Filament length: About 3 mm. Filament color: Blue/violet.

*Pistils.*—Pistil number: 1. Style color: 83A. Style length: About 6 mm. Receptacle height: About 4 mm. Receptacle width: About 2 mm.

Disease resistance: Under commercial conditions, resistance or susceptibility to pathogens of Saintpaulias has not been observed.

Seed production: Seed production is rarely observed.

It is claimed:

1. A new and distinct Saintpaulia plant named 'Moonbeam', as illustrated and described.

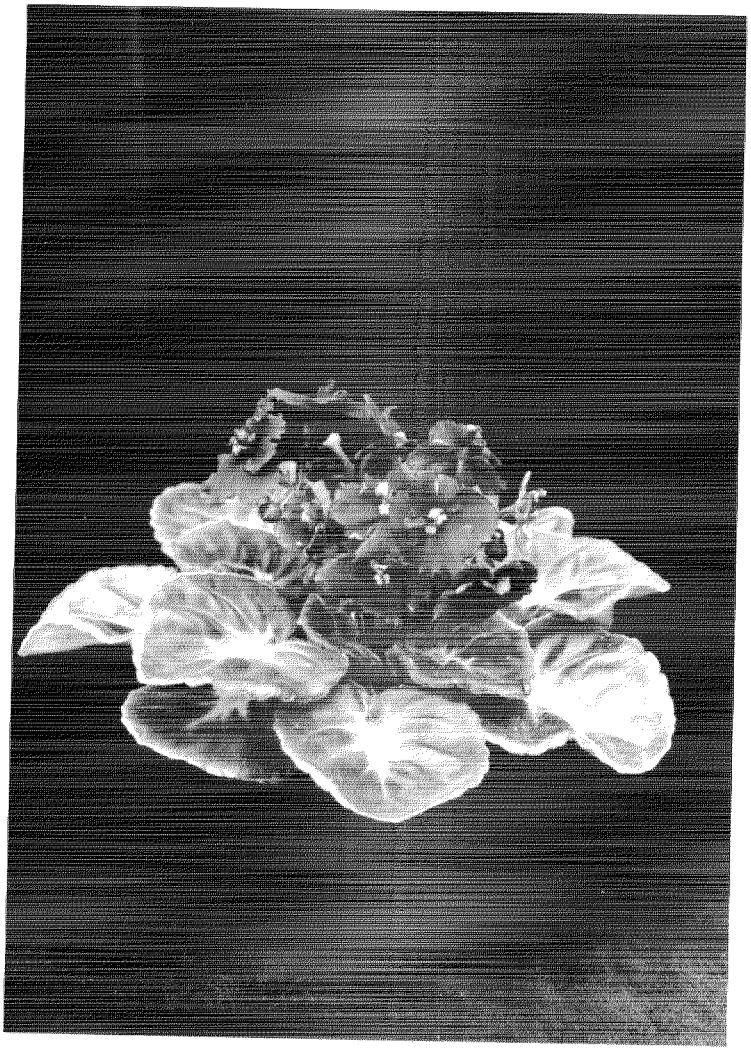

* * * * *